(12) United States Patent
Hacker et al.

(10) Patent No.: US 8,690,330 B2
(45) Date of Patent: Apr. 8, 2014

(54) DEVICE FOR SWEPT-SOURCE OPTICAL COHERENCE DOMAIN REFLECTOMETRY

(75) Inventors: Martin Hacker, Jena (DE); Ralf Ebersbach, Schmoelln (DE); Thomas Pabst, Stadtroda (DE); Ulf Peterlein, Jena (DE); Gerard Antkowiak, Jena (DE); Roland Bergner, Jena (DE); Ingo Koschmieder, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 225 days.

(21) Appl. No.: 13/140,752

(22) PCT Filed: Dec. 21, 2009

(86) PCT No.: PCT/EP2009/009189
§ 371 (c)(1),
(2), (4) Date: Jun. 17, 2011

(87) PCT Pub. No.: WO2010/072394
PCT Pub. Date: Jul. 1, 2010

(65) Prior Publication Data
US 2011/0255054 A1 Oct. 20, 2011

(30) Foreign Application Priority Data
Dec. 23, 2008 (DE) .......................... 10 2008 063 225

(51) Int. Cl.
*A61B 3/10* (2006.01)

(52) U.S. Cl.
USPC .......................................... 351/221; 351/246

(58) Field of Classification Search
USPC ........... 351/205, 246, 211; 356/497, 477, 511
See application file for complete search history.

(56) References Cited

U.S. PATENT DOCUMENTS

| | | | |
|---|---|---|---|
| 5,321,501 A | 6/1994 | Swanson et al. | |
| 6,160,826 A | 12/2000 | Swanson et al. | |
| 6,779,891 B1 | 8/2004 | Barth et al. | |
| 7,380,939 B2 | 6/2008 | Barth et al. | |
| 7,433,046 B2 | 10/2008 | Everett et al. | |
| 7,695,140 B2 | 4/2010 | Fercher | |

(Continued)

FOREIGN PATENT DOCUMENTS

| | | |
|---|---|---|
| DE | 43 09 056 A1 | 9/1994 |
| DE | 103 23 920 A1 | 12/2004 |

(Continued)

OTHER PUBLICATIONS

Choma, Michael A., et al., "Sensitivity advantage of swept source and Fourier domain optical coherence tomography," *Optics Express*, vol. 11, No. 18, Sep. 8, 2003, pp. 2183-2189.

(Continued)

*Primary Examiner* — Hung Dang
(74) *Attorney, Agent, or Firm* — Patterson Thuente Pedersen, P.A.

(57) ABSTRACT

A device for swept-source optical coherence domain reflectometry (SS OCDR) on moveable samples, particularly human eyes, for obtaining A-scans, having a measuring range according to the sample length and having a laser light source which can be adjusted by a main wave number $k_0$ and at least one receiver for the light dissipated from the sample, wherein the sample is illuminated on the sample surface by a measurement beam having a diameter D by way of a coupling device. The light source has a spectral line width of $\delta k < 168$ m$^{-1}$ and the adjustment of the light source is carried out in $\tau < 44$ s/(D*$k_0$).

38 Claims, 3 Drawing Sheets

(56) References Cited

U.S. PATENT DOCUMENTS

| | | |
|---|---|---|
| 7,982,881 B2 | 7/2011 | Fercher et al. |
| 2004/0239943 A1 | 12/2004 | Izatt et al. |
| 2006/0244973 A1* | 11/2006 | Yun et al. ..................... 356/511 |
| 2007/0291277 A1 | 12/2007 | Everett et al. |
| 2008/0037608 A1 | 2/2008 | Zhou et al. |
| 2008/0100612 A1 | 5/2008 | Dastmalchi et al. |
| 2008/0180685 A1 | 7/2008 | De Lega et al. |

FOREIGN PATENT DOCUMENTS

| | | |
|---|---|---|
| EP | 1 391 781 A1 | 2/2004 |
| EP | 1 870 030 A1 | 12/2007 |
| WO | WO 00/33729 | 6/2000 |
| WO | WO 2004/111661 A2 | 12/2004 |
| WO | WO 2005/047813 A1 | 5/2005 |
| WO | WO 2006/015717 A1 | 2/2006 |
| WO | WO 2006/058735 A1 | 6/2006 |
| WO | WO 2007/016296 A2 | 2/2007 |
| WO | WO 2007/065670 A2 | 6/2007 |
| WO | WO 2007/133961 A2 | 11/2007 |
| WO | WO 2008/086017 A1 | 7/2008 |
| WO | WO 2008/089393 A2 | 7/2008 |
| WO | WO 2008/154460 A1 | 12/2008 |

OTHER PUBLICATIONS

Yun, S.H., et al., "High-speed optical frequency-domain imaging," *Optics Express*, vol. 11, No. 22, Nov. 3, 2003, pp. 2953-2963.

Lexer, F., et al., "Wavelength-tuning interferometry of intraocular distances," *Applied Optics*, vol. 36, No. 25, Sep. 1, 1997, pp. 6548-6553.

Hitzenberger, Christoph K., et al., "In vivo intraocular ranging by wavelength tuning interferometry," *SPIE*, vol. 3251, 1998, pp. 47-51.

Yun, S.H., et al., "Motion artifacts in optical coherence tomography with frequency-domain ranging," *Optics Express*, vol. 12, No. 13, Jun. 28, 2004, pp. 2977-2998.

Srinivasan, V.J., et al., "High-speed, high-resolution optical coherence tomography retinal imaging with a frequency-swept laser at 850 nm,"*Optics Letters*, vol. 32, No. 4, Feb. 15, 2007, pp. 361-363.

Hammer, Daniel X., et al., "Active retinal tracker for clinical optical coherence tomography systems," *Journal of Biomedical Optics*, vol. 10(2), Mar./Apr. 2005, pp. 024038-1-024038-11.

Grajciar et al., "Improved sensitivity measurement of the human eye length in vivo with Fourier domain optical coherence tomography", Proc. of SPIE, vol. 6844, 2008, 8 pages.

Lee et al., "In vivo optical frequency domain imaging of human retina and choroid", Optics Express, May 15, 2006, vol. 14, No. 10, 9 pages.

* cited by examiner

DEVICE FOR SWEPT-SOURCE OPTICAL COHERENCE DOMAIN REFLECTOMETRY

PRIORITY CLAIM

The present application is a National Phase entry of PCT Application No. PCT/EP2009/009189, filed Dec. 21, 2009, which claims priority from German Application No 102008063225.2, filed Dec. 23, 2008, the disclosures of which are hereby incorporated by reference herein in their entirety.

FIELD OF THE INVENTION

The invention relates to a device for swept source optical coherence domain reflectometry such as can be applied in the optical biometry of the eye, for example.

BACKGROUND

The optimal matching of an artificial intraocular lens requires knowledge of the optical conditions in the patient's eye, in particular the distances between the cornea, crystalline lens and retina.

After this determination of position was originally carried out by means of ultrasound, a device operating optically and without making contact has been introduced in the form of the IOL Master of Carl Zeiss. The functional principle is based in this case on the so called time domain optical coherence domain reflectometry, a short coherence interferometry method such as is described, for example, in WO 00/33729, the content of which is incorporated by reference herein. The main component is a Michelson interferometer that enables the detection of interference of light scattered back by the cornea, lens and retina. The use of a short coherence light source means that it is possible for always only short wave chains to interfere with one another, and this determines the measuring accuracy. So that axial movements of the patient do not falsify the measurement result, the so called dual beam method is applied in which the light scattered back by the cornea serves as reference.

Since the measuring range that must be more than 43 mm for an eye (typical eye lengths vary between approximately 20 and 32 mm, extreme ones between 14 and 40 mm, the mean refractive index being approximately 1.36), must be traversed mechanically by the reference mirror in the case of Michelson interferometer, a measurement usually lasts a few seconds in which the patient is, for example, not allowed to blink since the eyelid movement would render the measurement impossible.

Efforts to accelerate the rate of adjustment of the reference path, for example, by rotating prisms such as EP 1 391 781, have not been successful, since the sensitivity is not sufficient to achieve the required measuring accuracy.

In DE 43 09 056 describes another measurement method based on short coherence, in the case of which light from a broadband light source is shone into the sample, and the light scattered back from various depths is analyzed spectrally. The depth information is obtained from a Fourier transformation of the detected signal. This method is denoted as spectral domain OCDR (SD ODCR) or, because of the Fourier transformation used, also as Fourier domain OCDR (FD OCDR). This category also includes the swept source OCDR (SS OCDR), which is described in the article entitled "High-speed optical frequency-domain imaging" by S. H. Yun et al., Optics Express 2003, page 2953, and in which the light source is tuned spectrally, and the signal received by the detector likewise includes the depth information after the Fourier transformation. As already shown in U.S. Pat. No. 5,321,501 for time domain OCT (TD OCT), the imaging required to implement optical coherence tomography (OCT) is implemented by Galvo scanners that deflect the measurement beam laterally over the sample.

Along the lines of the terminology introduced in the case of the ultrasound measuring device, the one-dimensional (axial) measurement in the case of OCDR along the light axis is generally denoted as an A-scan in general, and therefore also below. Likewise along the lines of the ultrasound terminology, the two-dimensional measurement with the aid of a lateral component in the case of OCT is also denoted as a B-scan.

A first attempt to apply SS OCDR in optical biometry was described in F. Lexer, C. K. Hitzenberger, A. F. Fercher and M. Kulhavy "Wavelength-tuning interferometry of intraocular distances", Appl. Optics 36 (1997) pages 6548-6553. This solution showed that it is possible in principle to measure the intraocular distances in the eye, although the measuring accuracy was much too inaccurate at 0.82 mm.

An improvement to this solution was disclosed in C. K. Hitzenberger, M. Kulhavy, F. Lexer, A. Baumgartner "In-vivo intraocular ranging by wavelength tuning interferometry", SPIE [3251-6] 1998. Here, a resolution of 0.15 mm was reached, but it still does not correspond to the requirements. The measuring accuracy for the eye length must, however, be smaller than 30 µm in order to limit the residual errors of the determined IOL refraction to ⅒ diopters.

In particular, the OCDR and OCT methods on moving samples such as, for example, the human eye have the problem that the sample can move during the measurement and this, as discussed in S. H. Yun et al. (2004), OPTICS EXPRESS 2977, can greatly reduce the signals and falsify them. The usual approaches to eliminating the problem are the extremely complicated tracking methods in which the movement of the sample is detected and the measurement beam position is tracked.

Such approaches to the compensation of typical movements of a few hundred micrometers per second are described, for example, in Hammer et al. (2005), Journal of Biomedical Optics 10(2), 024038, and in US 2006/105903. It is disadvantageous of such approaches that, despite the large technical outlay, the finite latency time of such systems always results in certain tracking errors, particularly for very fast eye movements such as saccades.

SUMMARY OF THE INVENTION

Proceeding from the prior art, it is therefore the object of the invention to specify a device with the aid of which the intraocular distances in the eye can be measured quickly and accurately, particularly even given the occurrence of typical eye movements, without exhibiting the disadvantages of an active measurement beam tracking with a sample movement such as, for example, latency time errors.

This object is achieved by a device for swept source optical coherence domain reflectometry (SS OCDR) on movable samples, particularly human eyes, for the purpose of obtaining A-scans, having a measuring range corresponding to the sample length and having a laser light source tunable about a centroid wave number $k_0$ and at least one receiver for the light backscattered from the sample, the sample being illuminated via a coupling device on the sample surface with the aid of a measurement beam of diameter D, in that the light source has a spectral line width of $\delta k < 168$ m$^{-1}$, and in that the tuning of the light source is performed in $\tau < 44$ s (D*$k_0$).

Distances are therefore measured with low expenditure and efficiently over the entire length of the eye since, despite typical eye movements of up to 1000 μm/s and given only moderate requirements for the tuning rate of the source, determine interfering signal losses resulting from sample displacements are avoided in the case of distance measurements between surfaces of the crystalline lens, cornea and retina.

The result of the inventive solution is therefore that the tuning time of the laser is matched to the sensible measurement beam profiles in the sample so that the lateral sample displacements possible during the tuning time of the laser can predominantly amount only to fractions of the smallest possible measurement beam diameter in the sample. Interfering signal losses, in turn, are therefore avoided by averaging out different lateral interference modulations, since the sample volumes illuminated at various instances during the tuning of the measurement beam have a sufficient overlap.

What is understood here by sensible measurement beam profiles are those that can supply signal strengths of cornea, crystalline lens and retina that suffice for spacing apart by virtue of the fact that they have measurement beam waist positions in the region between the back of the crystalline lens of relatively short eyes as far as to the retina of long eyes (8 . . . 40 mm).

At the same time, the inventive solution also avoids a signal reduction and signal corruption through axial sample displacements during tuning, for example extension or compression of the A-scan with resulting unacceptable errors in the spacing apart of the eye structures.

Thus, it is predominantly undisturbed signals that result, without the need for active tracking of the measurement beam with sample movements.

It is advantageous in this case when the light source has a spectral tuning range $\Delta k$ about a centroid wave number $k_0$ of at least $\Delta k > 18\,000\ m^{-1}$.

In this case the ratio of the tuning range $\Delta k$ and line width $\delta k$ is advantageously greater than 360, further preferably greater than 2000, further preferably greater than 4000, and yet further preferably greater than 9000. This ratio ensures the implementation of an adequate ratio between the measurement depth and measurement resolution.

A further advantage results when the quotient of the tuning rate $(\Delta k/\tau)$ and laser line width $\delta k$ is greater than 18 kHz, preferably also greater than 4 MHz, with further preference greater than 40 MHz.

It is particularly advantageous in this case when the detection of the light backscattered by the cornea, crystalline lens and retina is performed during a single tuning of the light source. It is advantageous here when the backscattered light detected at the receiver is digitized at a rate of more than $\Delta k$ $(\tau*\delta k)$. This ensures that the spectral information is adequately scanned.

The inventive device is particularly suitable when the line width $\delta k$ of the light source lies between 22 and 50 $m^{-1}$. Such line widths can be implemented, for example, with tunable fiber ring lasers, and offer acceptable drops in sensitivity over the measurement depth.

It is advantageous when the bandwidth of the at least one receiver, described, for example, by the cutoff frequency with 3 dB signal drop, is greater than $2*\Delta k/(\tau*\delta k)$ and preferably less than 80 MHz.

According to the invention, the device for SS OCDR on the eye is a tunable laser source, an interferometer with a reference arm and a sample arm closed off from the sample, detectors at the interferometer outputs, and a signal processing unit for the detected signals.

According to the invention, the position of retina signals and cornea signals in the A-scan, and the laser line width $\delta k$ are matched to one another in the device for SS-OCDR on the eye.

It is also particularly preferred to use a reference interferometer for wave number references of the source, and thus for length calibration of the OCDR signal.

It is particularly advantageous for the device for SS OCDR on the eye when the measurement beam diameter D is smaller than 3 mm in the region of the sample entrance.

It is also preferred for the measurement beam to be convergent before entering the eye, it preferably being possible to set or switch over the size of the convergence. Particularly, by setting the convergence it is possible to match to one another, or to optimize the relative strength of the detected signal from various eye regions (retina, lens, cornea) to facilitate a joint processing for measuring distance and visual evaluation of the signals.

Alternatively, it can also be advantageous when the measurement beam is collimated before entering the eye, and means are provided for refixation the eye, in order to be able to detect specula cornea signals and lens signals. Owing to the refixation, it is possible to measure on the optical axis of the eye, which can deviate by up to 14° from the visual axis.

It is also advantageous when it is possible to switch over between a collimated and a convergent measurement beam.

A further advantageous implementation of the invention results when the measurement beam strikes the eye outside the corneal apex, it being preferred to provide for the purpose of positioning the measurement beam relative to the eye an apparatus that can be driven, in particular, by evaluating the light detected by the receiver. This prevents a strong reflection by the corneal apex from saturating the detection apparatuses, or else prevents the signal-to-noise ratio from being degraded, for example by the increase in the shot noise component caused by the strong cornea reflection.

Such an apparatus for positioning the measurement beam, particularly when synchronized with the tuning of the laser, permits B-scans to be obtained and therefore permits the implementation of OCT over the entire eye. Such positionings of the measurement beam can, for example, be performed by optical configurations known per se in combination with angle deviations by galvanometer scanners, which are likewise known (U.S. Pat. No. 5,321,501).

It is particularly advantageous when a photon flux of $3*10^8$ to $1*10^{13}$ is directed onto the sample in the tuning time $\tau$ of the light source. Phototoxic effects can be avoided by suitable selection of the wavelength (for example 1016 nm). It is thereby possible to implement a high sensitivity for the weakly scattering eye structures by optimizing the signal-to-noise ratio caused by the shot noise, without there being damage to the eye tissue.

It can, furthermore, be advantageous when the measurement is performed along the visual axis of the eye since, in particular, the distance information on this axis is very valuable for matching intraocular lenses. To this end, the measurement beam and fixer light should strike the eye collinearly, but they can also have different divergences, for example in order to compensate a possible refraction error of the eye.

An advantageous refinement of the invention results when monomode fibers are used in the reference arm and/or source arm and/or detection arm and/or reference interferometer, in order to avoid disturbing parasitic interferences between different modes propagating in the fiber and artifacts resulting therefrom. Equally, the open fiber ends are designed as obliquely polished surfaces in order to avoid interfering retroreflections.

It is advantageous when the reference signals and sample signals are digitized at a constant scanning rate, it being preferred to use the same scanning rates for reference signals and sample signals. However, in order to reduce the data volume that occurs, it is also possible, given a suitable selection of the reference interferometer, to scan the reference signal at a lower scanning rate than the scanning of the sample signal.

According to the invention, the measurement beam has a wavelength of between 600 and 1150 nm, wavelengths of 700 nm, 800 nm and 1060 nm being particularly preferred.

A preferred refinement of the device for SS OCDR on the eye results in the fact that an apparatus is provided for projecting onto the eye, particularly the cornea, aiming markers with a wavelength of between 400 and 1500 nm and an observation unit is provided for detecting the reflections of these aiming markers. These can also be evaluated with regard to the determination of the position and shape of the cornea and lens.

It is further advantageous in this case when the observation unit, for example a camera, is provided for checking the adjustment of the measurement beam relative to the eye, the observation unit preferably being sensitive to the wavelengths of the measurement beam and the aiming markers. Cameras with a silicon sensor seem to be particularly suitable here because of their adequate residual sensitivity in the near infrared.

A particularly suitable refinement of the invention results when the light source is movable relative to the eye, light source and reference interferometer preferably being firmly connected.

Another advantageous condition for implementing the invention consists in that the interferometer is movable relative to the eye, light source and interferometer preferably being firmly connected.

It is advantageous in this case when the electrical and optical connections are designed to be separable.

The inventive device renders it possible for the first time to measure an entire eye with the aid of the OCDR method in an A-scan with an accuracy of better 100 µm, particularly better than 30 µm, in order thus to obtain measured values for matching an intraocular lens. Here, the measurement can comprise two or more simultaneous distance measurements between the cornea, lens and retina, and is robust against the usual axial and lateral patient movements, which typically lie in the region of 1 mm/s.

BRIEF DESCRIPTION OF THE DRAWINGS

The invention is explained in more detail below with the aid of drawings, in which FIGS. 1, 1a, 1b and 1c depicts a basic design of the inventive device, FIGS. 2, 2a, 2b, 2c and 2d depicts an example embodiment of the invention.

DETAILED DESCRIPTION

Figure 1:
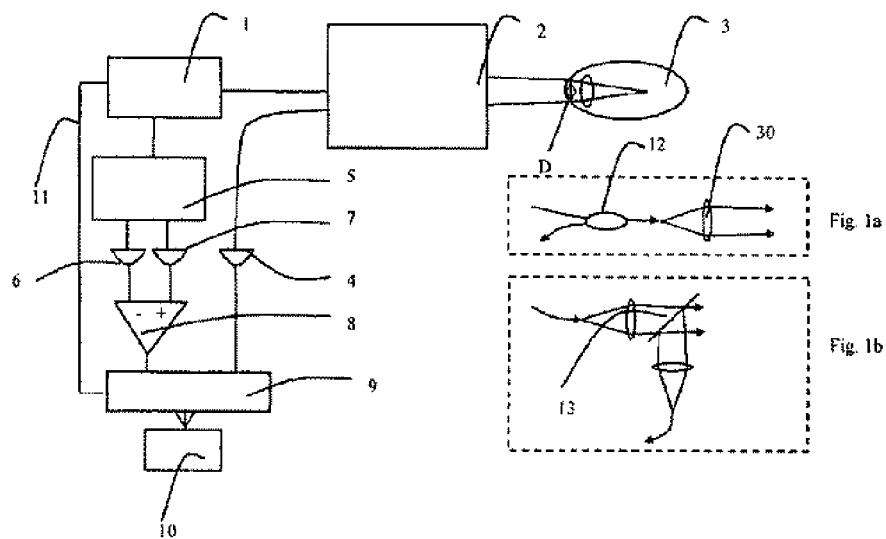

The basic design for implementing the invention in FIG. 1 consists of a suitable tunable laser 1 that is characterized by the following variables: tuning time $\tau$, wavelength $\lambda$, spectral tuning range $\Delta k$, centroid wave number $k_0$, and laser line width $\delta k$.

A beam shaping and coupling unit 2 serves both to direct the beam of the laser 1 onto the sample 3 (illustrated schematically here as an eye), and to feed the light backscattered by the sample 3 to a detector 4, D in this case being the diameter of the measurement beam when it impinges on the sample (here the cornea of the eye). Assigned to the laser 1 is a reference interferometer 5 whose preferred two detectors 6, 7 are connected to a data acquisition apparatus 9 via a difference amplifier 8. The detectors consist of InGaAs photodiodes with chip diameters >0.1 mm and bandwidths less than 80 MHz.

Here, the reference interferometer 5 is a fiber optic Mach-Zehnder interferometer having two outputs connected to the detectors 6 and 7. The optical path length difference between the arms of the reference interferometer is LREF. The arms of the reference interferometer 5 can consist of fibers with various chromatic dispersions so that the same dispersion is implemented in both arms despite wavelength difference, in order to attain a maximum modulation contrast at the detectors 6 and 7. It is also possible in principle to detect signals with the aid of only one detector 6 and without the difference amplifier 8, the signal quality being reduced.

The data acquisition apparatus 9 is likewise connected to the detector 4 of the light backscattered by the sample 3, and to the control and evaluation unit 10. This connection permits the control and evaluation unit 10 to acquire and process the signals received from the detector 4 and recorded with the aid of the data acquisition apparatus 9, and also permits synchronization of the measurement cycle between the data acquisition apparatus 9 and control and evaluation unit 10. Furthermore, there is provided between the data acquisition apparatus 9 and laser 1 a synchronization connection 11 with the aid of which the tuning of the laser 1 is synchronized with the data acquisition. The data acquisition apparatus 9 is thereby also capable of transmitting control signals to the laser 1 or of receiving them therefrom, if the laser carries out periodic tuning independently.

As illustrated in FIG. 1a, in this case the beam shaping and coupling unit 2 can be designed with a fiber coupler 12, while an implementation with a beam splitter 13 is also possible, as shown in FIG. 1b.

The control and evaluation unit 10 controls the tuning of the laser 1 via the data acquisition apparatus 9 (with a spectral tuning range $\Delta k$ in the tuning time $\tau$), and the light backscattered by the sample 3 and measured by the detector 4 is digitized and subjected in a known way to a Fourier transformation, for example a discrete Fourier transformation DFT, for the reconstruction of the A-scan.

Figure 1C:
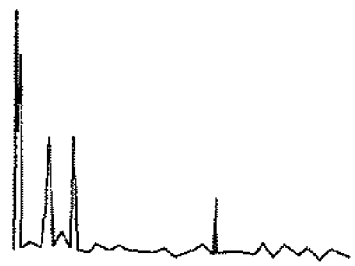

In this case, the reconstruction of the A-scan is particularly performed in such a way that the interpolation point spacing in the A-scan is smaller than $4*\ln 2/\Delta k$, in particular smaller than $4/3*\ln 2/\Delta k$. If the coupling element 2 does not include a further apparatus for generating a reference light component, an autocorrelation signal is obtained as an A-scan, in a manner similar to that described by K. Hitzenberger, A. F. Fercher and M. Kulhavy in "Wavelength-tuning interferometry of intraocular distances", Appl. Optics 36 (1997), pages 6548 to 6553. This A-scan, which is symmetrical along the light propagation axis about the strongest signal component (mostly the cornea surface signal) can be trimmed so that redundant information is omitted (FIG. 1c).

The reference interferometer 5 serves in this case to determine the timing of the tuning process exactly. To this end, a simultaneous recording of the reference interferometer signal and measurement signal with the aid of the data acquisition apparatus 9 permits the instantaneous, relative wave numbers of the laser to be assigned very exactly to the measurement signals.

In particular, it is possible thereby to interpolate measurement signals for any interpolation point systems in the spectral domain (remapping), for example in order, with reference to equidistant wave numbers into specific tissues, to obtain A-scans with a constant resolution over the entire measurement depth range after the Fourier transformation. Furthermore, a numerical compensation of the chromatic dispersion reducing the resolution is also possible thereby. Such a remapping and these dispersion compensations are described in U.S. Pat. No. 7,330,270 for SD-OCT, the entire content thereof is incorporated by reference.

As described in V. J. Srininivasan et al. Optics Letters 32, 361, equidistant wave numbers can be obtained by way of example in this case via a phase reconstruction of the signals from the reference interferometer 5 by means of Hilbert transformation with subsequent determination of equidistant phase spacings.

It is further necessary to this end to ensure that statistical errors in the tuning of the wave number of the laser source 1 are so small that the phases of the signals from the reference interferometer 5 can be uniquely reconstructed. It is to hold true, particularly, that the standard deviation of the wave number error $\sigma_k$ remain below a limit $\sigma_k < \pi/(LREF \cdot v)$ prescribed by the length LREF, so that phase errors>$\pi$ can, for example, occur only every 400 (v=4.05) . . . 10 000 (v=3.23) scans.

The OCDR signals can also be improved by averaging and subtracting background signals that can be obtained without a sample, or with the measurement beam masked out.

FIG. 1c shows the A-scan obtained for the example of an eye as sample 3, that is to say the longitudinal profile along the light axis. The peaks show from left to right in this case the reflections of the cornea, front side of the lens, rear side lens and retina.

Figure 2:
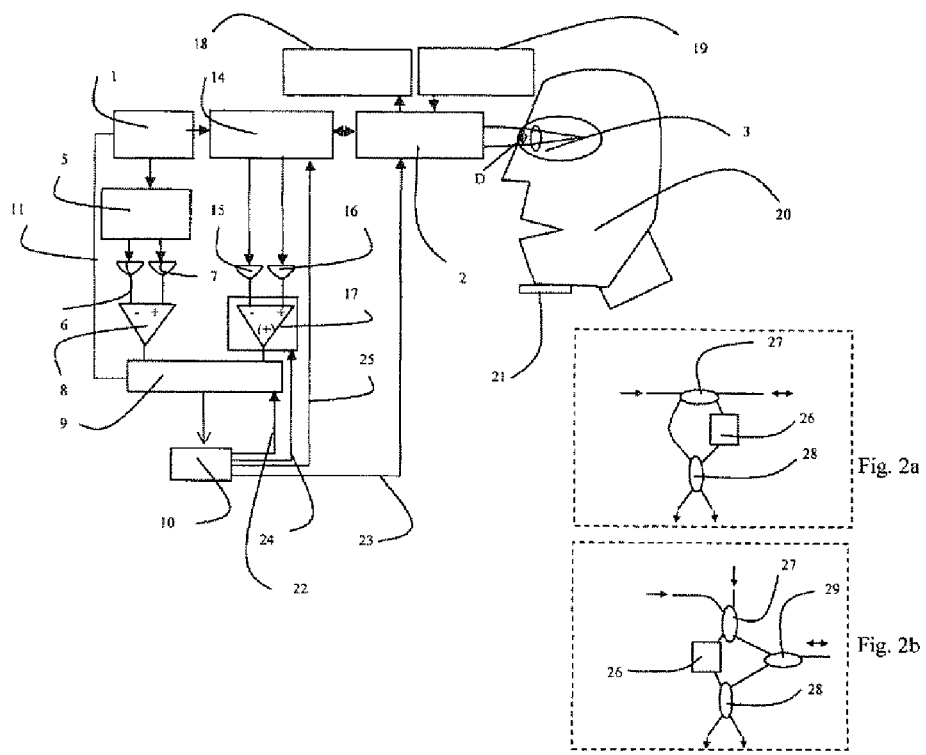

FIG. 2 shows an example embodiment of the invention for biometry of the eye. The basic design consisting of a tunable laser source 1, beam shaping and coupling unit 2, reference interfometer 5 with the detectors 6, 7, the assigned difference amplifier 8 and the data acquisition unit 9 corresponds to the design known from FIG. 1. In addition, there is arranged downstream of the laser 1 a further interferometer 14, which implements interference of light shone into the sample 3 (eye) and backscattered with a reference light component that can then be detected with the aid of the detectors 15 and 16. Assigned to the two detectors 15, 16 of the interferometer 14 is an amplifier 17 that can, in a particular embodiment, be switched over between difference amplification and aggregate gain. The output of the amplifier 17 is connected, in turn, to the data acquisition unit 9.

The fundamental signal processing, that is to say, by way of example, the detection of the signals from the reference interferometer 5, the remapping, the background subtraction and the Fourier transformation, is performed here in the same way as described previously for the obtaining of the auto correlation signals.

In this case, the reference light component is generated by means of a transmissive reference arm in an interferometer 14 consisting of fiber optic components. Alternatively, it is also possible to use reference light components obtained via a reflection, for example at fiber ends. FIGS. 2a and 2b show two variants of such a fiber interferometer. An adjustable attenuator 26 that permits the reference light component to be set for a favorable response of the detectors 15 and 16 is used, furthermore, in the reference arm of these interferometers. Possible polarization compensators in the sample arm or reference arm that enables a partial or complete compensation of the polarization states of the reference light and sample light for the purpose of adequate interference, are not illustrated.

The first fiber coupler 27 serves the purpose of division into a sample arm and reference arm.

The division ratio of the fiber coupler 27 is set in this case in FIG. 2a so that the predominant portion of the light returning from the sample is fed to the detectors 15 and 16.

The fiber coupler 28 serves the purpose of interferometrically superposing the reference light from the reference arm on the returning sample light, and of feeding the signal components of opposite phase to the detectors 15 and 16 for balanced detection. In principle, it is also possible to use the options, described in WO 2004/111 661, to determine further quadrature components for mirror artifact supposition in FD-OCDR.

In FIG. 2b, the fiber coupler 27 effects a part of the reference arm attenuation, and the fiber coupler 29 is selected in such a way that light returning from the sample is fed predominately to the detectors 15 and 16. This is advantageous when the adjustable attenuator 26 has only a limited attenuation range. Furthermore, visible light can still be fed in from the fixation light source 19 via the fiber coupler 27.

If the adjustable attenuator 26 is designed so that the reference light can also be completely blocked, it is consequently possible thereby also to obtain the above-mentioned autocorrelation signals. In this case, the amplifier 17 is switched over to summation while, given use of the reference light component for a balanced detection, it is necessary to switch over to subtraction. Given a reference arm that is not blocked, summation signals can also be used for laser monitoring.

It has proved to be effective for the measurement of the eye to select a measurement wavelength $\lambda$ in the infrared region, that is to say, for example, between 600 and 1150 nm, values such as 700 nm, 800 nm and 1060 nm being particularly preferred.

Furthermore, the arrangement has an observation camera 18 and a fixation source 19. The observation camera 18 corresponds to the CCD camera in WO 00/33729, the entire contents of which is incorporated herein by reference, and serves, as there, to control the alignment of the measurement arrangement relative to the eye 3 of the patient; to this end, it is also possible in addition to project aiming markers onto the eye. This means that they should have at least a residual sensitivity for the measuring wavelength $\lambda$ and this is generally valid for cameras with the silicon sensor (including in a CMOS fashion), in particular the comparatively strong reflection of the measurement beam at the cornea being effectively determinable. The fixation source 19 serves to align the eye relative to the measuring arrangement and can, for example, be designed in analogy with the proposal in DE 103 23 920, the entire contents of which is incorporated by reference. The patient can be influenced by exerting appropriate control so that measurement is performed optionally on the axis of the eye or the visual axis ("refixation").

For the measurement, the patient places his head 20 onto the test subject rest 21, in order for it to be held largely at rest. The laser 1 and interferometer 14 are interconnected in a stable position and can be displaced jointly with the aid of means (not illustrated here) in order to adjust with reference to the patient's eye 3. This stable position connection also proves to be advantageous when the light is guided via fibers, in particular monomode fibers. It is thereby particularly possible to dispense with the use of variable fiber optic polarization compensators (paddles).

The data acquisition unit 9 permits the digitization of signals from the amplifier 8 (signal from the reference interferometer 5) and from the amplifier 17 (signal from the interferometer 14) with different bit depths.

In order to reduce the data volume to be transmitted, the minimum bit depth MBT for the digitization of the reference interferometer signal is in this case matched to the optical wavelength difference LREF in the reference interferometer 5 and to the optical OCDR measuring range ZMAX in the following way: MBT>=log 2(2/(1−|cos(π*LREF/2ZMAX)|). Given an LREF=100 mm and a ZMAX=60 mm, what is MBT=4 bit.

Bit depths of <14 bit are used to digitize the OCDR signals from the interferometer 14, a bit depth of 10 bit, in particular, being adequate.

The control unit 10 is connected to the data acquisition unit 9 via a line 22 in order to enable a switchover of the bit depth of the measured signal. Such a bit depth switchover is, for example, advantageous for an optimum response upon switchover between autocorrelation measurement and measurement with the aid of the reference arm.

Furthermore, the control unit 10 is connected to the beam shaping and coupling unit 2 (line 23) in order to be able to implement a switchover of the focus (as in DE 103 23 920), while the amplifier 17 can be controlled via a further line 24, in particular can be switched over between the summation function and difference function. In addition, a switchover of the amplification ratio of the amplifier is performed, particularly given overdriving of the OCDR signals, or in the event of a switchover between autocorrelation measurement and measurement with reference to a reference light component from a reference arm.

For focusing purposes, the coupling unit 2 includes a focusing lens 30 that generates a measurement beam focus in the eye posterior to the front eye section (preferably 8 to 25 mm behind the cornea, at most 40 mm behind the cornea). Alternatively, it is also possible to use diffractive or reflective focusing elements. An adaptation to the refraction of the eye can also be performed in this case by suitable adaptation optics. It is advantageous here when the fixation source 19 is fed into the coupling unit 2 in such a way that the fixation is not influenced by the focusing of the measurement beam, and the best possible imaging of the fixing light on the retina results, that is to say preferably downstream of the focusing lens 30.

Furthermore, the coupling optics can also include an apparatus for displacing or deflecting the measurement beam, in particular in order to improve OCDR signals, for example by avoiding strong interfering corneal reflections by lateral measurement beam displacement.

Figures 2C, 2D:
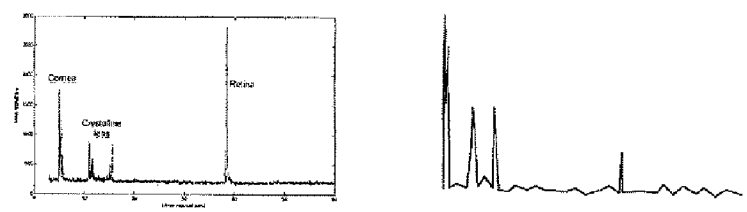

The switching over of the attenuation or blocking of the reference arm in the interferometer 14 is performed via a connection 25 between the control unit 10 and interferometer 14. FIG. 2c shows an A-scan that was measured with the aid of an arrangement according to FIG. 2 (with reference arm), while FIG. 2d shows an analogous measurement with a blocked reference arm, that is to say by means of determining the autocorrelation function of the backscattered sample light, without representation of the mirror-symmetric signal component.

With the preferred values of tuning range $\Delta k=112\,000\,m^{-1}$, $D=2$ mm, wavelength $\lambda=1060$ nm and tuning time $\tau=500\,\mu s$, it is possible for the first time to determine the overall eye length and the position of the crystalline lens in one measuring operation with an OCDR resolution/measuring accuracy of <30 μm. It is ensured here that the measurement result is not corrupted by involuntary eye movements.

It has emerged that the maximum laser line width δk depends on the measurement regime. The laser line width must be smaller than $162\,m^{-1}$ in the case of measuring the autocorrelation function, that is to say with a blocked reference arm.

If use is made of an arrangement with a reference arm, it is possible by suitable definition of the reference plane in the sample to ensure that: 1. the signals from the cornea, lens and retina are detected with sufficient strength, and that 2. mirror artifacts can be suppressed or identified and eliminated by computation. FIG. 3 shows this schematically for various positions of the reference plane, which can be set via the wavelength differences between the reference and sample light paths.

Figure 3A:
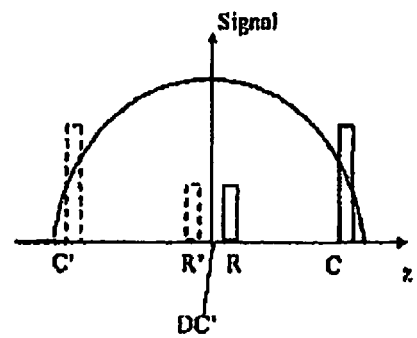
FIGS. 3a, 3b, 3c, 3d and 3e depicts various solutions for arranging the reference plane for the measurement.

In FIG. 3a, the reference plane was set behind the retina (R), the result being a maximum laser line width of $93\,m^{-1}$ (signal drop of 80 dB over a total measuring range of 54 mm, represented schematically as a curve). R'C' denote the mirror artifacts here and below.

Figure 3B:
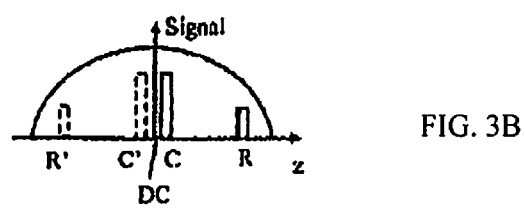

In FIG. 3b, the reference plane is set in front of the cornea (C), the result being a maximum laser line width of $81\,m^{-1}$ (possible signal drop of 60 dB over a total measuring range of 54 mm, since the cornea reflects better than the retina).

Figure 3C:
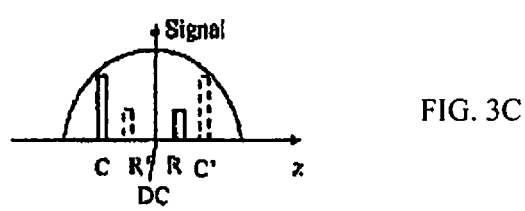

In FIG. 3c, the reference plane was set between the cornea (C) and retina (R), the result being a maximum laser line width of $162\,m^{-1}$.

Figure 3D:
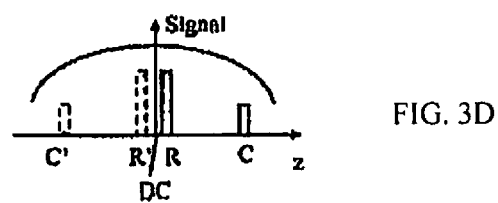

As in FIG. 3a, in FIG. 3d the reference plane was set behind the retina (R); given a target signal drop of only 20 dB over a total measuring range of 54 mm, the result is a maximum laser line width of $47\,m^{-1}$. This is the preferred laser line width δk. It is necessary here to implement a minimum space of 64 mm between the reference planes and the optical element that lies closest to the eye and is traversed by the measurement beam.

Figure 3E:
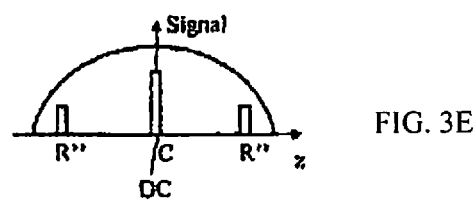

FIG. 3e shows the conditions in the case of the measurement of the autocorrelation function. For substantially narrower laser line widths ($<20\,m^{-1}$), there is the risk that signal artifacts could occur from reflections by the optical elements and corrupt the interpretation of the measurement results.

If the aim is to make joint use of measurement and mirror signals (FIG. 3c), or if there is a risk of undesired overlap between the measurement signals (for example, R, C in FIG. 3a, b), unique identification of the mirror signals (R', C') is required to avoid error.

It is preferred for this purpose to implement variations in the conditions of measurement or reconstruction in such a way as to perform unique variations in the mirror signal that permit a manual and automated identification, or else suppression.

A first example option for this is the variation in the difference between the lengths of reference arm and sample arm, which in the case of the mirror signal effects a local variation that is opposite to the measurement signal and can be detected numerically. This can be performed, for example, by varying the distance between the test subject and measuring apparatus, preferably in the range of 0.1 to 4 mm, and by determining the first moment of the signal distribution of the signal component to be identified. Alternatively, it is also possible to perform between successive tunings of the laser very quick phase shifts between the reference arm and sample arm by means of which it is possible to use the spectral data to reconstruct a complex FD-OCDR signal in the case of which it is also possible to suppress the mirror artifact completely or partially (compared to U.S. Pat. No. 7,433,046 B2). This complete or partial suppression of mirror artifacts is then also suitable as an identification feature. However, this procedure is more complicated and more sensitive to sample movements than the determination of relatively large local variations. A further option is the use of an unbalanced chromatic dispersion in accordance with U.S. Pat. No. 7,330,270, there subsequently being, however, a need to perform numerical reconstruction several times with different dispersion compensation coefficients in order to effect and determine different degrees of smearing of the measurement and mirror signals. In particular, a change in sign during the dispersion correction has the effect that smearing takes place from the mirror signal to the measurement signal, as a result of which it is likewise possible to perform an identification, for example by determining the second moment of the distribution of the signal component to be identified.

A further advantageous solution is to fundamentally avoid an undesired overlap between the measurement and mirror signals in such a way as to exclude a positioning of the interferometric reference plane in the region between the cornea and retina. One possible embodiment to this end is to design the interferometer so that the reference plane is always reliably positioned in front of the cornea of a test subject held in a head support (FIG. 3b), while the measuring range is selected to be sufficiently large in order to cover the positioning error and the eye length range, particularly by selecting an interferometric measuring range (one-sided A-scan length) of at least 44 mm. If the aim is to facilitate adjustment of the patient's eye, it is recommended to select an interferometric measuring range of at least 50 mm.

It is advantageous that in the case of the inventive solution it is possible not only to detect a single eye region, such as the front chamber or retina, by a B-scan, but that it is also possible simultaneously to obtain additional B-scan information from the respective other regions. This is particularly advantageous, since this additional information permits not only very accurate measurements of the spacing of the eye structures inside individual A-scans despite possible eye movements over the duration of the B-scan recording, but also allow the correction of the B-scan data for a reproduction of movement corrected image data. By way of example, it would be preferred for this purpose to record a B-scan of a retina region while the B-scan simultaneously includes image information of the cornea such as, for example, specular reflections from the front or rear surface of the cornea. Were there allowed to be axial eye movements of the test subject during the B-scan recording, these movements would jointly influence the profiles of the corneal and retinal structures. If the image information of the cornea is now corrected in such a way that it would correspond to a shape otherwise determined by measurement or recorded, the correction used to this end can also be applied to the image information corresponding to the retinal structures, and a movement corrected representation can likewise be attained thereby. By way of example, such a correction can be implemented by axial and lateral displacements of the A-scan forming the B-scan, particularly in such a way that the corneal structures in the image exhibit, for example, minimum deviations from a shape that is determined in advance by corneal keratometry or corneal topography and is, in particular, to be described by continuous functions.

An alternative correction option is to analyze the cornea profile with reference to its apparent local surface curvatures in the B-scan, and to derive modulation frequencies that can then be separated into components of shape and movement by plausibility considerations in order subsequently to reduce the movement component in the image data. This can preferably take place in such a way that at least one boundary surface of the cornea is determined, and the axial positions thereof are plotted relative to the lateral deflection or else the corresponding A-scan recording instances, and are transformed into a modulation frequency spectrum by Fourier transformation. Subsequently, shape and movement components can be obtained by a suitably fashioned filter. The movement components can subsequently be corrected by Fourier back transformation and oppositely directed displacement of the A-scans in the image data so that the cornea and retina as well as the front chamber appear with corrected movement. These abovementioned filters for the modulation frequencies can be obtained, for example, by analysis of clinical topography data, in a way known per se from U.S. Pat. No. 7,370,969, the entire content of which is hereby incorporated by reference.

The implementation of the invention is not tied to the example embodiment illustrated—expert developments do not go beyond the scope of protection of the patent claims.

The invention claimed is:

1. A device for swept source optical coherence domain reflectometry (SS OCDR) on a movable sample, for the purpose of obtaining A-scans, comprising:
   a tunable laser light source;
   at least one receiver for light backscattered from the sample, wherein the sample is illuminated on the sample surface with a measurement beam of diameter D;
   wherein the light source has a line width of $\delta k < 168$ m$^{-1}$,
   wherein the A scan measuring range corresponds to a depth of the sample and
   further wherein the device is configured such that tuning of the light source is performed in $\tau < 44$ sec/$(D*k_0)$ about a centroid wave number $k_0$.

2. The device for SS OCDR as claimed in claim 1, wherein the sample comprises a human eye.

3. The device for SS OCDR as claimed in claim 2, wherein the measurement beam is convergent before entering the eye.

4. The device for SS OCDR as claimed in claim 3, wherein a degree of the convergence is tuneable or switchable.

5. The device for SS OCDR as claimed in claim 2, wherein the measurement beam is colliminated before entering the eye, and further comprising means for refixation of the eye so that measurement is made on one of an optical axis of the eye and a visual axis of the eye.

6. The device for SS OCDR as claimed in claim 2, wherein the measurement beam is switchable between a colliminated and a convergent measurement beam.

7. The device for SS OCDR as claimed in claim 2, wherein the measurement beam strikes the eye outside a corneal apex.

8. The device for SS OCDR as claimed in claim 7, further comprising an apparatus that controls positioning the measurement beam relative to the eye.

9. The device for SS OCDR as claimed in claim 8, wherein the apparatus that controls the positioning of the measurement beam relative to the eye does so by evaluating the light detected by the receiver.

10. The device for SS OCDR as claimed in claim 2, wherein a photon flux of $3*10^8$ to $3*10^{13}$ is directed onto the eye during tuning of time $\tau$ of the light source.

11. The device for SS OCDR as claimed in claim 2, wherein measurement is performed along a visual axis of the eye.

12. The device for SS OCDR as claimed in claim 2, wherein detection of light backscattered by a cornea, a crystalline lens and a retina is performed during a tuning of the light source.

13. The device for SS OCDR as claimed in claim 2, wherein reference signals and sample signals are digitized at constant scanning rates.

14. The device for SS OCDR as claimed in claim 13, wherein the constant scanning rates for reference signals and sample signals are the same.

15. The device for SS OCDR as claimed in claim 2, wherein the light source is movable relative to the eye.

16. The device for SS OCDR as claimed in claim 15, further comprising a reference interferometer and wherein the light source and the reference interferometer are rigidly connected.

17. The device for SS OCDR as claimed in claim 16, wherein the reference interferometer has a wave number reference for length calibration of the OCDR signal.

18. The device for SS OCDR as claimed in claim 2, further comprising an interferometer that is movable relative to the eye, the light source and interferometer being rigidly connected.

19. A device for SS OCDR as claimed in claim 2 further comprising means for variation in one of measurement conditions and reconstruction conditions, the variation in one of the measurement conditions and the reconstruction conditions being undertaken so as to attain one of identification and suppression of a mirror artifact signal.

20. The device for SS OCDR as claimed in claim 19, wherein the means for variations in one of measurement conditions and reconstruction conditions comprises a unit for varying a path length difference between the sample arm and reference arm of the interferometer.

21. The device for SS OCDR as claimed in claim 1, wherein the light source has a spectral tuning range $\Delta k$ about a centroid wave number $k_0$ of at least $\Delta k > 18\,000$ m$^{-1}$.

22. The device for SS OCDR as claimed in claim 21, wherein the ratio of a tuning range $\Delta k$ and line width $\delta k$ is greater than 360.

23. The device for SS OCDR as claimed in claim 21, wherein a quotient of the tuning rate $\Delta k/\tau$ and laser line width $\delta k$ is greater than 18 kHz.

24. The device for SS OCDR as claimed in claim 21, wherein the backscattered light detected at the receiver is digitized at a rate of more than $\Delta k/(\tau*\delta k)$.

25. The device for SS OCDR as claimed in claim 1, wherein the line width $\delta k$ of the light source lies between 22 and 50 m$^{-1}$.

26. The device for SS OCDR as claimed in claim 1, wherein the bandwidth of the at least one receiver is greater than $2*\Delta k/(\tau*\delta k)$.

27. The device for SS OCDR as claimed in claim 26, wherein the bandwidth of the at least one receiver is less than 80 Mhz.

28. The device for SS OCDR as claimed in claim 1, further comprising an interferometer with a reference arm.

29. The device for SS OCDR as claimed in claim 28, wherein the position of retina signals and cornea signals in the A-scan and the laser line width $\delta k$ are matched to one another.

30. The device for SS OCDR as claimed in claim 1, wherein the measurement beam diameter D is smaller than 3 mm.

31. The device for SS OCDR as claimed in claim 1, further comprising monomode fibers in at least one of a reference arm, a source arm, a detection arm, and a reference interferometer.

32. The device for SS OCDR as claimed in claim 1, wherein the measurement beam has a wavelength of between 600 and 1150 nm.

33. The device for SS OCDR as claimed in claim 1, further comprising an apparatus for projecting onto the eye aiming markers with a wavelength of between 400 and 900 nm.

34. The device for SS OCDR as claimed in claim 33, further comprising a camera for checking adjustment of the measurement beam relative to the eye.

35. The device for SS OCDR as claimed in claim 34, wherein the camera is sensitive to the wavelengths of the measurement beam and the aiming markers.

36. A method for SS OCDR on the eye, comprising:
   detecting and evaluating light backscattered by a cornea from individual tunings of a light source with regard in each case to time dependent cornea positions;
   comparing the time dependent cornea positions with an expected profile; and
   using deviations from the expected profile to correct position data of cornea, crystalline lens and/or retina.

37. A method for SS OCDR on the eye, as claimed in claim 3, further comprising deflecting a measurement beam laterally at one of during individual tunings and between the individual tunings.

38. A method for SS OCDR on the eye, as claimed in claim 36, further comprising
   illuminating the eye with a measurement beam of diameter D from a tunable laser light source; and
   detecting light backscattered by a cornea, a crystalline lens and a retina during a tuning of the tunable laser light source wherein the light source has a line width of $\delta k < 168$ m$^{-1}$, and
   further wherein tuning of the light source is performed in $\tau < 44$ sec/(D*$k_0$) about a centroid wave number $k_0$.

* * * * *

UNITED STATES PATENT AND TRADEMARK OFFICE
CERTIFICATE OF CORRECTION

PATENT NO. : 8,690,330 B2  Page 1 of 1
APPLICATION NO. : 13/140752
DATED : April 8, 2014
INVENTOR(S) : Hacker et al.

It is certified that error appears in the above-identified patent and that said Letters Patent is hereby corrected as shown below:

In the Claims

Claim 29, Col. 14, line 8, delete "6k" and insert --δk--

Signed and Sealed this
Twenty-ninth Day of July, 2014

Michelle K. Lee
*Deputy Director of the United States Patent and Trademark Office*

(12) EX PARTE REEXAMINATION CERTIFICATE (10902nd)
United States Patent
Hacker et al.

(10) Number: US 8,690,330 C1
(45) Certificate Issued: Jun. 27, 2016

(54) DEVICE FOR SWEPT-SOURCE OPTICAL COHERENCE DOMAIN REFLECTOMETRY

(75) Inventors: Martin Hacker, Jena (DE); Ralf Ebersbach, Schmoelln (DE); Thomas Pabst, Stadtroda (DE); Ulf Peterlein, Jena (DE); Gerard Antkowiak, Jena (DE); Roland Bergner, Jena (DE); Ingo Koschmieder, Jena (DE)

(73) Assignee: CARL ZEISS MEDITEC AG, Jena (DE)

Reexamination Request:
No. 90/013,544, Jul. 6, 2015

Reexamination Certificate for:
Patent No.: 8,690,330
Issued: Apr. 8, 2014
Appl. No.: 13/140,752
PCT Filed: Dec. 21, 2009
PCT No.: PCT/EP2009/009189
§ 371 (c)(1),
(2), (4) Date: Jun. 17, 2011
PCT Pub. No.: WO2010/072394
PCT Pub. Date: Jul. 1, 2010

Certificate of Correction issued Jul. 29, 2014

(30) Foreign Application Priority Data

Dec. 23, 2008 (DE) .......................... 10 2008 063 225

(51) Int. Cl.
*A61B 3/10* (2006.01)
*G01N 21/47* (2006.01)
*G01B 9/02* (2006.01)

(52) U.S. Cl.
CPC ............... *A61B 3/1005* (2013.01); *A61B 3/102* (2013.01); *G01B 9/0203* (2013.01); *G01B 9/02004* (2013.01); *G01B 9/02067* (2013.01); *G01B 9/02069* (2013.01); *G01B 9/02091* (2013.01); *G01N 21/4795* (2013.01); *G01B 2290/45* (2013.01)

(58) Field of Classification Search
None
See application file for complete search history.

(56) References Cited

To view the complete listing of prior art documents cited during the proceeding for Reexamination Control Number 90/013,544, please refer to the USPTO's public Patent Application Information Retrieval (PAIR) system under the Display References tab.

*Primary Examiner* — Kenneth J Whittington

(57) ABSTRACT

A device for swept-source optical coherence domain reflectometry (SS OCDR) on moveable samples, particularly human eyes, for obtaining A-scans, having a measuring range according to the sample length and having a laser light source which can be adjusted by a main wave number $k_0$ and at least one receiver for the light dissipated from the sample, wherein the sample is illuminated on the sample surface by a measurement beam having a diameter D by way of a coupling device. The light source has a spectral line width of $\delta k < 168$ m$^{-1}$ and the adjustment of the light source is carried out in $\tau < 44$ s/(D*$k_0$).

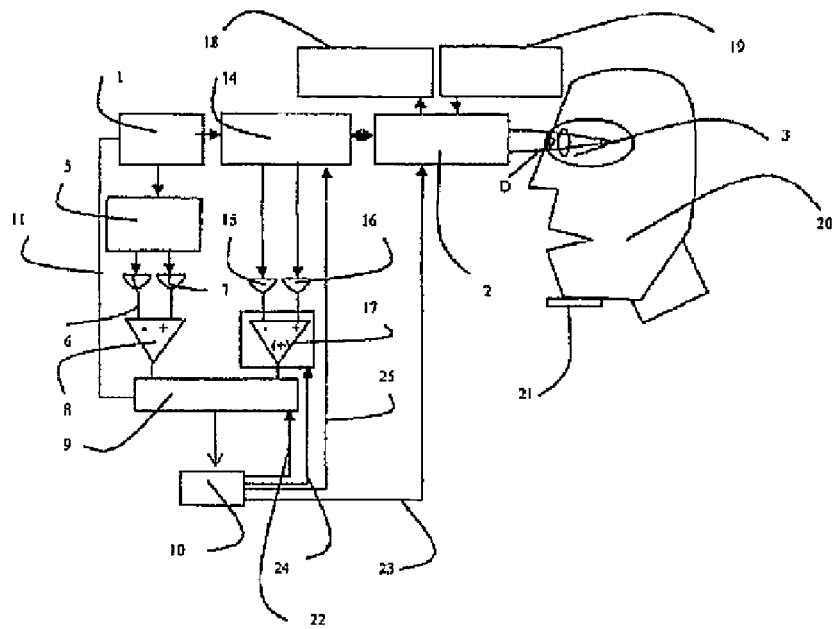

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 36 and 38 is confirmed.

Claim 1 is determined to be patentable as amended.

Claims 2-35, dependent on an amended claim, are determined to be patentable.

New claims 39-43 are added and determined to be patentable.

Claim 37 was not reexamined.

1. A device for swept source optical coherence domain reflectometry (SS OCDR) on a movable sample, for the purpose of obtaining A-scans, comprising:
   a tunable laser light source;
   at least one receiver for light backscattered from the sample, wherein the sample is illuminated on the sample surface with a measurement beam of diameter D;
   wherein the light source has a line width of $\delta k < 168 \ m^{-1}$, *wherein $k = 2\pi/\lambda$,*
   wherein the A scan measuring range corresponds to a depth of the sample, and
   further wherein the device is configured such that tuning of the light source is performed in *a time* $\tau < 44 \ sec/(D*k_0)$ about a centroid wave number $k_0$.

39. *A device for swept source optical coherence domain reflectometry (SS OCDR) on a movable sample, wherein the sample comprises a human eye, for the purpose of obtaining A-scans, comprising:*
   *a tunable laser light source;*
   *at least one receiver for light backscattered from the sample, wherein the sample is illuminated on the sample surface with a measurement beam of diameter D;*
   *wherein the light source has a line width of $\delta k < 168 \ m^{-1}$, wherein the A scan measuring range corresponds to a depth of the sample, and further wherein the device is configured such that tuning of the light source is performed in $\tau < 44 \ sec/(D*k_0)$ about a centroid wave number $k_0$, and wherein a photon flux of $3*10^8$ to $3*10^{13}$ is directed onto the eye during the tuning time $\tau$ of the light source.*

40. *The device for SS OCDR as claimed in claim 2, wherein $\delta k < 93 \ m^{-1}$.*

41. *The device for SS OCDR as claimed in claim 40, wherein a reference plane is set behind a retina of the eye.*

42. *The device for SS OCDR as claimed in claim 2, wherein $\delta k < 162 \ m^{-1}$.*

43. *The device for SS OCDR as claimed in claim 42, wherein a reference plane is set between a cornea and a retina of the eye, or an autocorrelation function is measured.*

* * * * *